(12) United States Patent
Inada et al.

(10) Patent No.: US 11,072,822 B2
(45) Date of Patent: Jul. 27, 2021

(54) RNA AMPLIFICATION METHOD, RNA DETECTION METHOD AND ASSAY KIT

(71) Applicant: KABUSHIKI KAISHA TOSHIBA, Minato-ku (JP)

(72) Inventors: Mika Inada, Tokyo (JP); Koji Hashimoto, Atsugi (JP); Keiko Ito, Kawasaki (JP)

(73) Assignee: KABUSHIKI KAISHA TOSHIBA, Minato-ku (JP)

( * ) Notice: Subject to any disclaimer, the term of this patent is extended or adjusted under 35 U.S.C. 154(b) by 369 days.

(21) Appl. No.: 15/908,044

(22) Filed: Feb. 28, 2018

(65) Prior Publication Data
US 2018/0274022 A1 Sep. 27, 2018

(30) Foreign Application Priority Data
Mar. 21, 2017 (JP) .............................. JP2017-054577

(51) Int. Cl.
*C12Q 1/68* (2018.01)
*C12Q 1/6853* (2018.01)

(52) U.S. Cl.
CPC ................................ *C12Q 1/6853* (2013.01)

(58) Field of Classification Search
CPC ............ C12Q 1/6853; C12Q 2521/107; C12Q 2525/207; C12Q 2525/101; C12Q 2527/101
See application file for complete search history.

(56) References Cited

U.S. PATENT DOCUMENTS

| | | |
|---|---|---|
| 2004/0058378 A1 | 3/2004 | Kong et al. |
| 2006/0154286 A1 | 7/2006 | Kong et al. |
| 2008/0227104 A1 | 9/2008 | Hayashizaki et al. |
| 2010/0092971 A1 | 4/2010 | Okamoto et al. |
| 2013/0177915 A1 | 7/2013 | Too et al. |
| 2014/0356874 A1* | 12/2014 | Bearinger ............ C12Q 1/6846 435/6.12 |
| 2016/0362732 A1 | 12/2016 | Takahashi et al. |
| 2017/0218455 A1* | 8/2017 | Steelman ............. C12Q 1/6844 |
| 2018/0282792 A1 | 10/2018 | Ito et al. |
| 2018/0363043 A1 | 12/2018 | Hashimoto et al. |

FOREIGN PATENT DOCUMENTS

| | | |
|---|---|---|
| JP | 2008-526231 A | 7/2008 |
| JP | 2009-171935 | 8/2009 |
| JP | 2013-530698 | 8/2013 |
| JP | 2019-53 | 1/2019 |
| WO | WO 2015/076356 A1 | 5/2015 |
| WO | WO 2017/158840 A1 | 9/2017 |

OTHER PUBLICATIONS

Sanghamitra Bandyopadhyay et al. "Development of the Human Cancer MicroRNA Network", Silence, A Journal of RNA Regulation, vol. 1, No. 6, 2010, 14 pages.

Ze-Hua Wang et al. "Research Progress of MicroRNA in Early Detection of Ovarian Cancer", Chinese Medical Journal, vol. 128, Issue 24, Dec. 20, 2015, pp. 3363-3370.

Thermo Fisher Scientific Inc., "Product Information: Bsm DNA Polymerase, Large Fragment", 2016, 3 pages, downloaded by the JPO on Apr. 24, 2018 from: https://assets.fishersci.com/TFS-Assets/LSG/manuals/MAN0012034_Bsm_DNAPolymerase_Large_Fragment_UG.pdf.

OptiGene, "Tin(exo-) LF DNA Polymerase", Feb. 23, 2017, 8 pages, downloaded by the JPO on Apr. 24, 2018 from: http://www.optigene.co.uk/tinexo-If-dna-polymerase.

Tsugunori Notomi, et al., "Loop-mediated isothermal amplification of DNA", Nucleic Acids Research, 2000, vol. 28, No. 12, 7 pages.

* cited by examiner

*Primary Examiner* — David C Thomas

(74) *Attorney, Agent, or Firm* — Oblon, McClelland, Maier & Neustadt, L.L.P.

(57) ABSTRACT

In general, according to one embodiment, a method containing, reverse-transcribing the first sequence in the target RNA, to obtain a reverse-transcription product containing a first' sequence complementary to the first sequence, dissociating the reverse-transcription product from the target RNA, hybridizing an elongation primer and the reverse-transcription product to elongate both, thereby obtain an elongation product, and maintaining the amplification reaction liquid containing the elongation product, a primer set and Tin(exo-) DNA polymerase and/or Bsm DNA polymerase under an amplification reaction condition, to amplify the first' sequence.

24 Claims, 6 Drawing Sheets

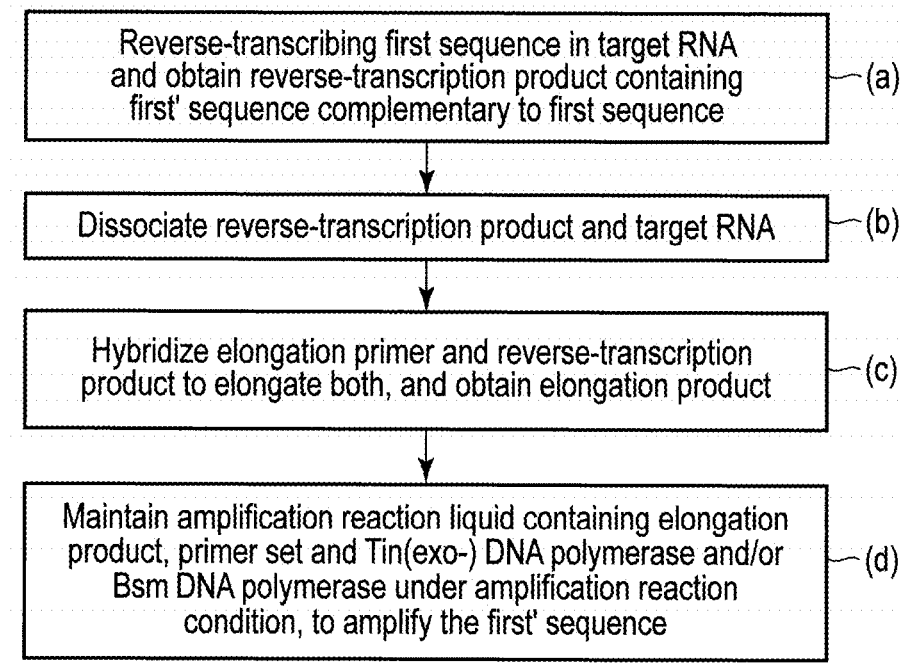
F I G. 1
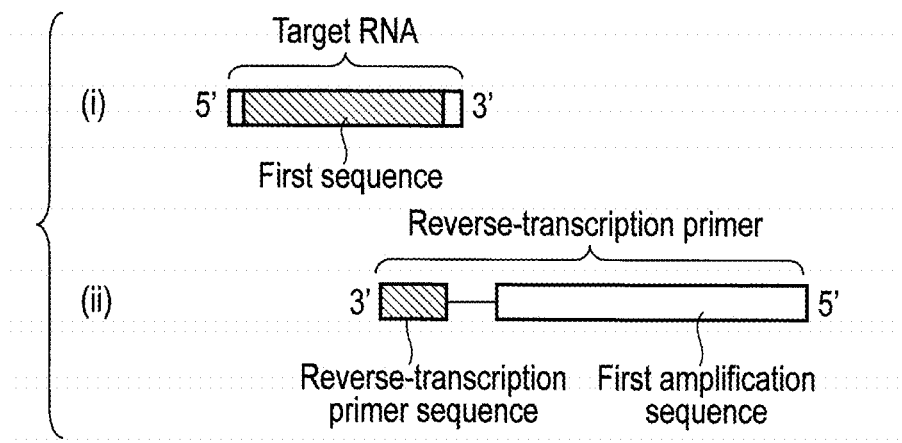
F I G. 2

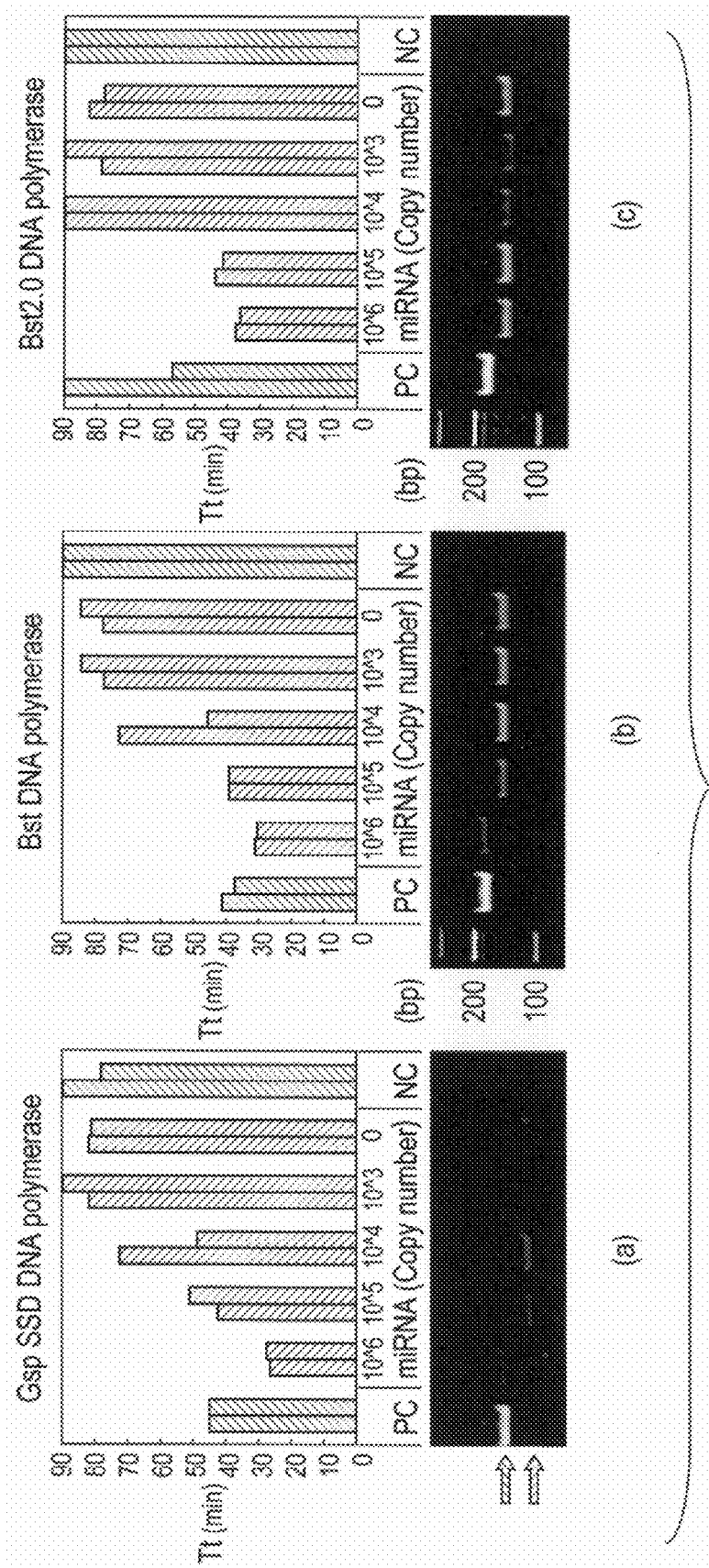
F I G. 9

RNA AMPLIFICATION METHOD, RNA DETECTION METHOD AND ASSAY KIT

CROSS-REFERENCE TO RELATED APPLICATIONS

This application is based upon and claims the benefit of priority from Japanese Patent Application No. 2017-054577, filed Mar. 21, 2017, the entire contents of which are incorporated herein by reference.

FIELD

Embodiments described herein relate generally to an RNA amplification method, an RNA detection method, and an assay kit.

BACKGROUND

MicroRNA (miRNA) is a kind of RNA which does not code a protein, but serves to, for example, control expression of genes or proteins. The latest research shows that there is a correlation between the amount of expression of miRNA and each of various diseases including cancer. Therefore, miRNA is expected as a new biomarker to diseases. Generally, the detection of miRNA is carried out by the Northern blotting, microarray or real time PCR. But, since miRNA is a short single-stranded RNA of about 20 bases, it is difficult to amplify or detect it, or to improve the sensitivity of the detection. Under such circumstances, there is a demand for development of an miRNA detection method with higher accuracy.

BRIEF DESCRIPTION OF THE DRAWINGS

FIG. 1 is a flowchart illustrating an example of an RNA amplification method of an embodiment.

FIG. 2 is a conceptual diagram showing an example of a target RNA and a reverse-transcription primer.

FIG. 9 includes graphs and electropherograms showing test results of Example 1.

DETAILED DESCRIPTION

Figure 3:
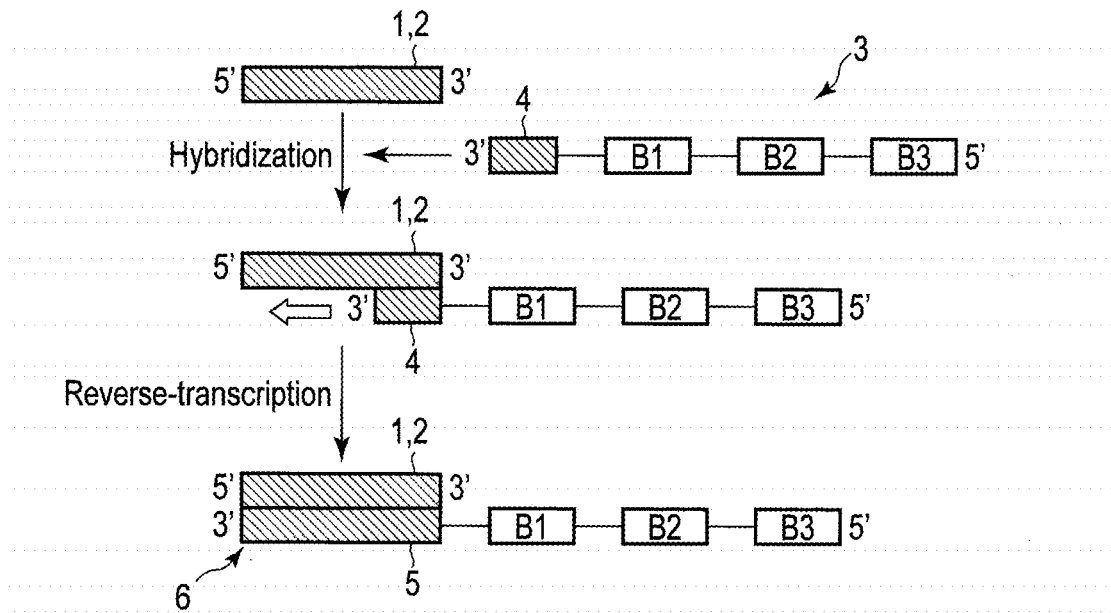
FIG. 3 is a conceptual diagram showing an example of a process of producing a reverse-transcription product.

In general, according to one embodiment, a method of amplifying a target RNA containing a first sequence, in a sample, comprises the following steps. In step (a), the first sequence in the target RNA is reverse-transcribed, thereby obtaining a reverse-transcription product containing a first' sequence complementary to the first sequence. In step (b), the reverse-transcription product and the target RNA are dissociated from each other. In step (c), an elongation primer and the reverse-transcription product are hybridized to elongate both, thereby obtaining a double-stranded DNA elongation product containing the first' sequence and/or the complementary sequence. In step (d), the amplification reaction liquid containing the elongation product, a primer set to be bound to the elongation produce and at least one of Tin(exo-) DNA polymerase and Bsm DNA polymerase are maintained under an amplification reaction condition, thereby amplifying the first' sequence and/or the complementary sequence.

Various embodiments will be described below with reference to the accompanying drawings. Each figure is an exemplary diagram of an embodiment to aid understanding of the embodiment. The shapes, dimensions or ratios in the drawings may differ from those of the actual device, and may be appropriately changed in light of the subsequent explanation and the known art.

1. RNA Amplification Method

The RNA amplification method according to the embodiment is a method of amplifying a target RNA in a sample, which contains a first sequence.

The target RNA is RNA to be detected in the RNA amplification method of the embodiment. The target RNA preferably is a single-stranded short-chain RNA having a base length of about 50 bases or less. The short-chain RNA may be, for example, a functional RNA such as microRNA (miRNA), small interfering RNA (siRNA), small nuclear RNA (snRNA) or small nucleolar RNA (snoRNA), or may not be a functional RNA, or may be an artificial RNA or an RNA produced by fragmenting RNA longer than 50 bases.

The target RNA contains a first sequence. The first sequence is a sequence which can serve as an indicator for detecting the target RNA. That is, the first sequence is a target of reverse-transcription reaction in the RNA amplification method of the embodiment. Note that the first' sequence, which is a complementary sequence to the first sequence, and a complementary sequence thereto, produced by reverse-transcription of the first sequence are the targets of the amplification reaction in the RNA amplification method of the embodiment. For example, the first sequence may be a sequence contained in the target RNA and also specific to the target RNA. The first sequence may be the sequence ranging over the entire length of the target RNA, or a partial continuous sequence selected from the sequence ranging over the entire length of the target RNA. The base length of the first sequence can be, for example, 3 to 10 bases, 10 to 20 bases, 20 to 30 bases, 30 to 40 bases, or 40 to 50 bases, and preferably 10 to 50 bases.

Here, the term "amplification" refers to continuously reproducing a template nucleic acid using a primer set and an enzyme. The amplification method employable in the embodiment can be any amplification method conventionally well-known by itself which amplifies nucleic acid using a primer set. The amplification method may be, for example, an isothermal amplification method. The isothermal amplification method may be, for example, LAMP, SMAP, RCA, ICAN or the like, although it is not limited to these.

The RNA amplification method of the embodiment will be described with reference to FIG. 1. FIG. 1 briefly shows the flow of the RNA amplification method.

In step (a), the first sequence is reverse-transcribed, and thus a reverse-transcription product containing the first' sequence complementary to the first sequence is obtained.

Step (a) may be carried out by, for example, maintaining a reverse-transcription reaction liquid under a reverse-transcription reaction condition. The reverse-transcription reaction liquid includes a sample, a reverse-transcription primer and a reverse transcriptase.

The sample is an object to be analyzed and is one which may contain the target RNA. The sample may be, for example, a material such as blood, serum, leukocyte, lymph, spinal fluid, urine, feces, semen, sweat, saliva, oral mucosa, expectoration, lacrimal fluid, mother milk, amniotic fluid, tissue, biopsy, isolated cells or cultured cells extracted from an animal, or an organ, isolated cells or cultured cells or an extract from a plant, or a mixture containing microbe, bacteria, fungus or virus, or an environmental material extracted from environment, a mixture containing synthetic RNA, or a material itself of a mixture containing any of these. Or it may be a formulation prepared from any of these materials.

The animal may be, for example, a mammal, bird, amphibian, reptile, fish, or arthropod, or some other living organism belonging to the animal kingdom. The mammal may be any of a primate such as an ape or human, a rodent such as a mouse or rat, a companion animal such as a dog, cat or rabbit, or a livestock such as a horses, cow or pig.

It is preferable that the sample be in a state that does not interfere with the amplification reaction. Being in such a state, it is possible to amplify the target RNA more efficiently in the RNA amplification method of the embodiment. The state which does not interfere with the amplification reaction is defined as, for example, that in which the kind of an ingredient in the sample, a combination of ingredients, or the concentration of an ingredient does not decrease the amplification reaction speed, or delay or stop the reaction.

When the material itself, described above is in the state which does not interfere with the amplification reaction, the material may be used directly as a sample. Or, for example, the obtained material may be subjected to a pretreatment conventionally well-known by itself to obtain a sample of the state which does not interfere with the amplification reaction or of a more suitable state for the amplification. The pretreatment is, for example, mincing, homogenization, centrifuging, precipitation, extraction and/or separation.

For example, the extraction may be carried out with use of a commercially available nucleic acid extraction kit. Usable examples of the nucleic acid extraction kit are ureLink (registered trademark) miRNA Isolation Kit (of Thermo Fisher Scientific), microRNA Extractor(registered trademark) SP Kit (of Wako Pure Chemical Industries, Ltd.), NucleoSpin (registered trademark) miRNA (of Takara Bio Inc.), mirpremier (registered trademark) microRNA Isolation Kit (of Sigma-Aldrich Co.), High Pure miRNA Isolation Kit (of Roche Life Science, Ltd.) and PAXgene Blood miRNA Kit (of Qiagen, Ltd.), but are not limited to these. Alternatively, a sample may be obtained without using such a kit, but by, for example, diluting the material with a buffer solution, followed by heat-treatment at 80° C. to 100° C. and extraction by centrifuging the resultant and collecting the supernatant.

The reverse-transcription primer is a primer of a single-stranded DNA to reverse-transcribe the first sequence. FIG. 2 shows an example of the target RNA and the reverse-transcription primer of the embodiment. The target RNA (i) contains the first sequence. The reverse-transcription primer (ii) contains a reverse-transcription primer sequence and a first amplification sequence. The reverse-transcription primer sequence and the first amplification sequence are contained in the reverse-transcription primer in this order from a 3' to a 5' direction. The full length of the reverse-transcription primer should preferably be 20 to 80 bases.

The reverse-transcription primer sequence is a sequence which serves as a primer for reverse-transcribing the first sequence. The base sequence of the reverse-transcription primer sequence is a sequence complementary to a desired sequence on the target RNA, which is selected so that the first sequence of the target RNA (i) can be reverse-transcribed over its full length. The reverse-transcription primer sequence is, for example, a sequence complementary to a continuous sequence containing a 3' terminal of the first sequence on the target RNA. Or, when the first sequence is selected to have a desired number of sequences between a 3' terminal of the target RNA and a 3' terminal of the first sequence as shown in FIG. 2, part (i), the reverse-transcription primer sequence may be complementary to the sequence between the 3' terminal of the first sequence and the 3' terminal of the target RNA (not shown). The base length of the reverse-transcription primer sequence may be 5 to 20 bases, though not particularly limited, but preferably, 7 to 15 bases, or more preferably, 8 to 12 bases.

The first amplification sequence is a sequence noncomplementary to the first sequence, and contains a sequence or a complementary sequence thereof, which may be bound to at least one primer contained in the primer set to which bound to the elongation product, which will be described later. Besides such a sequence, the first amplification sequence may contain a predetermined sequence, which may be, for example, such a sequence that the sequence itself or a complementary sequence thereof is necessary for the amplification reaction in the RNA amplification method of the embodiment. The base length of the first amplification sequence should preferably be, for example, 20 to 60 bases.

For example, after designing, in advance, the base sequence of the primer contained in the primer set to be bound to the elongation product in step (c), which will be described later, based on the structure and base sequence of the primer, the base sequence of the first amplification sequence may be designed. Or, a DNA sequence of a desired length may be selected as the first amplification sequence, and the primer set to be bound to the elongation product may be designed based on the base sequence thereof.

A spacer sequence may be present between the reverse-transcription primer sequence and the first amplification sequence. The base length of the spacer sequence should preferably be, for example, 4 to 16 bases.

The reverse transcriptase may be any of the well-known types, and selected according to, for example, the type of the reverse-transcription primer and/or the type or sequence of the target RNA. Examples of the reverse transcriptase are M-MuLV reverse transcriptase, AMV reverse transcriptase, transcriptor reverse transcriptase, SuperScript (registered trademark) transcriptor reverse transcriptase, or MultiScribe reverse transcriptase, though not limited to these.

The reverse-transcription reaction liquid may contain, in addition to these ingredients, ingredients necessary for the reverse-transcription reaction. Such ingredients may be, for example, a substrate such as a salt or deoxynucleoside triphosphates (dNTPs), a thickening agent as a reaction reagent, a buffer material for adjusting pH, a surfactant, an ion which increases the annealing specificity and or an ion which gives rise to a cofactor of reverse transcriptase, etc.

The reverse-transcription reaction liquid described above is maintained under reverse-transcription reaction conditions. The reverse-transcription reaction conditions may be selected depending on the type of the reverse-transcription primer, the type of the target RNA and/or the type of the reverse transcriptase, etc., based on the common knowledge of a person having ordinary skilled in the art. Examples of the conditions for the reverse-transcription reaction may be a temperature of 45° C. or less and for 15 minutes to 1 hour.

When the reverse-transcription reaction liquid is maintained under these conditions, the first sequence is reverse-transcribed, and a reverse-transcription product containing the first' sequence complementary to the first sequence is obtained.

FIG. 3 shows an example of the process of producing a reverse-transcription product. The example shown in FIG. 3 is the case where the LAMP method is used in the RNA amplification method of the embodiment.

First, a reverse-transcription primer sequence 4 of a reverse-transcription primer 3 hybridizes with a first sequence 2 of a target RNA 1. The reverse-transcription primer 3 contains the reverse-transcription primer sequence 4, and a B1 sequence, a B2 sequence and a B3 sequence as the first amplification sequence, in this order. The B1 sequence, B2 sequence, and B3 sequence are designed based on, for example, the LAMP primer set used in a later step of the isothermal amplification. The LAMP primer set includes a BIP primer containing a B2 sequence and a B1c sequence, an FIP primer containing an F2 sequence and an F1c sequence, a B3 primer containing a B3 sequence and an F3 primer containing an F3 sequence (not shown). Here, the terms "B1 sequence", "B2 sequence", "B3 sequence", "F1 sequence", "F2 sequence" and "F3 sequence" are used in the same meanings as those used by a person skilled in the art when designing a LAMP primer. Further, the B1c sequence is complementary to the B1 sequence, and the F1c sequence is complementary to the F1 sequence. The B2 sequence in the first amplification sequence is a complementary sequence of a sequence to which the B2 sequence of the BIP primer binds. The B3 sequence in the first amplification sequence is a complementary sequence of a sequence to which the B3 sequence of the B3 primer binds. The B1 sequence in the first amplification sequence is a sequence necessary for producing an amplification product in the LAMP reaction.

Next, with a reverse transcriptase (not shown), the elongation to the 3' terminal of the reverse-transcription primer sequence 4 in a 5' direction (indicated by hollow arrow), which uses the target RNA 1 as the template, advances. Thus, the first sequence 2 is reverse-transcribed to produce a first' sequence 5 complementary to the first sequence 2. As a result, a reverse-transcription product 6 which includes the first' sequence 5, the B1 sequence, B2 sequence and B3 sequence in this order is obtained. The reverse-transcription product 6 is hybridized with the target RNA 1.

Next, in a step (b), the reverse-transcription product and the target RNA are dissociated from each other. The dissociation may be carried out, for example, after the reverse-transcription reaction by heating the reverse-transcription reaction liquid to 80° C. to 100° C. With such heating, the reverse transcriptase may be deactivated at the same time as the dissociation of the RNA described above. Thus, it is possible to prevent the reverse-transcription reaction from adversely affecting the later steps after step (b).

Next, in step (c), the elongation primer and the reverse-transcription product are hybridized to elongate the elongation primer and the reverse-transcription product, thereby obtaining an elongation product of double-stranded DNA which contains the first' sequence and/or its complementary sequence.

Figure 4:
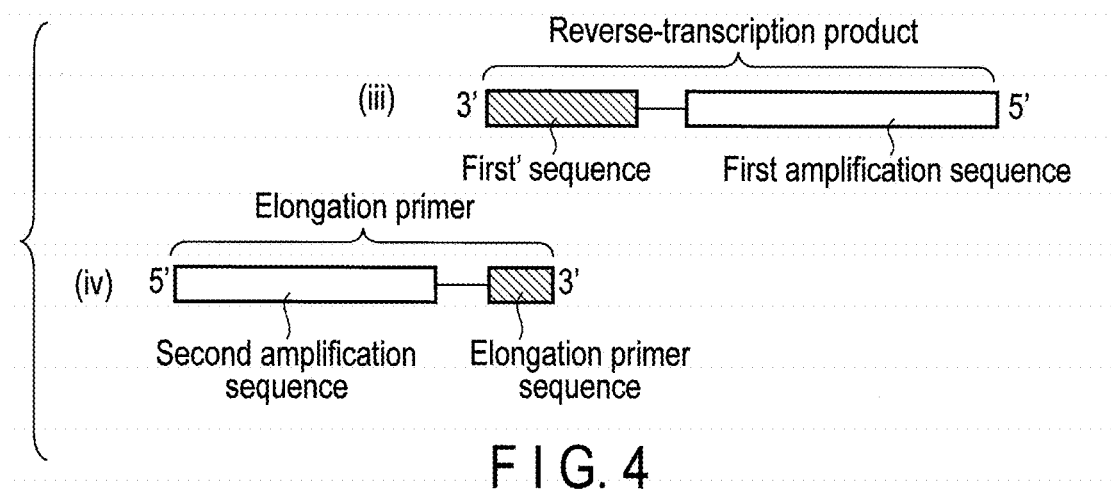
FIG. 4 is a conceptual diagram showing an example of a reverse-transcription product and an elongation primer.
Figure 5:
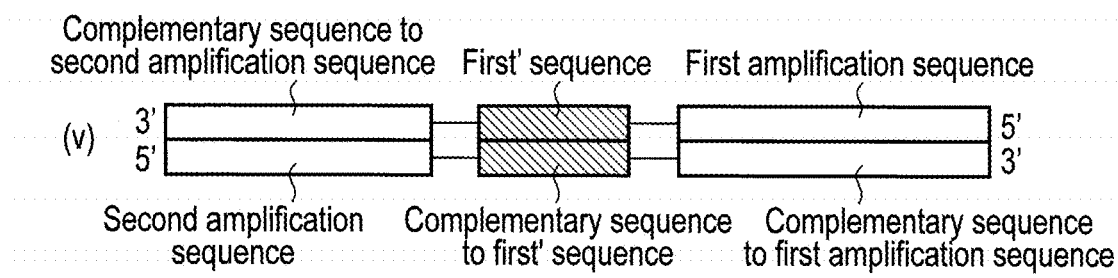
FIG. 5 is a conceptual diagram showing an example of an elongation product.

Step (c) will be described in more detail with reference to FIGS. 4, 5 and 6.

Step (c) may be carried out, for example, by maintaining the elongation reaction liquid under elongation reaction conditions. The elongation reaction liquid contains a reverse-transcription product obtained in steps (a) and (b), an elongation primer and a DNA polymerase.

The reverse-transcription product is a reverse-transcription product obtained in steps (a) and (b).

The elongation primer is a single-stranded DNA and is a primer which hybridizes with a reverse-transcription product for obtaining a double-stranded DNA which can be amplified in step (d). FIG. 4 shows an example of each of the reverse-transcription product and the elongation primer. The reverse-transcription product (iii) contains the first' sequence and the first amplification sequence. The elongation primer (iv) contains an elongation primer sequence and a second amplification sequence. The elongation primer sequence and the second amplification sequence are contained in the elongation primer in this order from the 3' toward 5' direction.

The elongation primer sequence is a sequence selected so as to be able to produce a complementary sequence of a sequence ranging over the entire length of the first' sequence using the first' sequence as the template, and it is a sequence complementary to a continuous sequence containing the 3' terminal of the reverse-transcription product (iii). The elongation primer sequence may also include a sequence complementary to a sequence of 5 bases or less, preferably, 3 bases or less, from the 3' terminal of the reverse-transcription primer to the 5' direction. The base length of the elongation primer sequence should preferably be, for example, 30 to 120 bases.

The second amplification sequence contains a sequence which is noncomplementary to the first' sequence, and also is to which a primer to be bound to the elongation product can bind, or complementary sequence thereof. The second amplification sequence may contain a predetermined sequence in addition to the sequence to which a primer contained in the primer set to be bound to the elongation product, which will be described later, can bind or a complementary sequence thereof. It may be, for example, a sequence, itself or a complementary sequence thereof, necessary for the amplification reaction. The base length of the second amplification sequence should preferably be, for example, 30 to 90 bases.

For example, after designing the base sequence of the primer set to be bound to the elongation product used at a step (c), based on the structure of the primer set, the base sequence of the second amplification sequence may be designed. Or, a DNA sequence of a desired length may be selected as the second amplification sequence, and the primer to be bound to the elongation product may be designed based on the base sequence thereof.

A spacer sequence may be present between each sequence pair of an elongation primer sequence and the second amplification sequence. The base length of the spacer sequence should preferably be, for example, 4 to 16 bases.

The DNA polymerase may be any well-known reverse DNA polymerase, and is selected according to the type of the elongation primer and/or the sequence of the reverse-transcription product, etc. Usable examples of such DNA polymerase are Klenow Fragment (Large Fragment E. coli DNA polymerase I), T4 DNA polymerase, phi29 DNA polymerase, Bst DNA polymerase, Csa DNA polymerase, 96-7 DNA Polymerase, Vent(exo-) DNA polymerase, Gsp SSD DNA polymerase, Tin exo-DNA polymerase, and also other DNA polymerases generally used for the PCR amplification including Taq DNA polymerase. Or, reverse transcriptases which can carry out the amplification using DNA as the template, such as M-MuLV Reverse Transcriptase, Transcriptor Reverse Transcriptase or the like can be used. Further, DNA polymerase may be at least one of Tin(exo-) DNA polymerase and Bsm DNA polymerase used in step (d), as will be described in detail.

In addition to these ingredients, the elongation reaction liquid may further contain a predetermined ingredient necessary for the elongation reaction. Such ingredients may be, for example, a substrate such as salt and dNTPs, a thickening agent as a reaction reagent, a buffer for adjusting pH, a surfactant, an ion that enhancing the annealing specificity, and/or an ion used as a cofactor of the reverse transcriptase.

The elongation reaction liquid described above is maintained under an elongation reaction condition. The elongation reaction condition may be selected depending on the type of the elongation primer, the type of the reverse-transcription product, and/or the type of the DNA polymerase, etc., based on the common knowledge of a person having an ordinary skill in the art. The reaction temperature of the elongation reaction is dependent on the type of enzyme, and is, generally, for example, 10° C. to 80° C. The elongation reaction can be carried out by maintaining the reaction temperature at constant, in a plurality of temperature zones each for a certain period of time, or repeating a plurality of temperature zones in a plurality of times of cycles.

By maintaining the elongation reaction liquid under these conditions, the elongation primer hybridizes to the reverse-transcription product, and the elongation primer and the reverse-transcription product elongate while utilizing each other as a template, and thus the elongation product of a double-stranded DNA can be obtained. FIG. 5 shows an example of the elongation product. One chain of the elongation product (v) contains a complementary sequence of the second amplification sequence, the first' sequence and the first amplification sequence, and the other chain contains the second amplification sequence, a complementary sequence of the first' sequence and a complementary sequence of the first amplification sequence.

Figure 6:
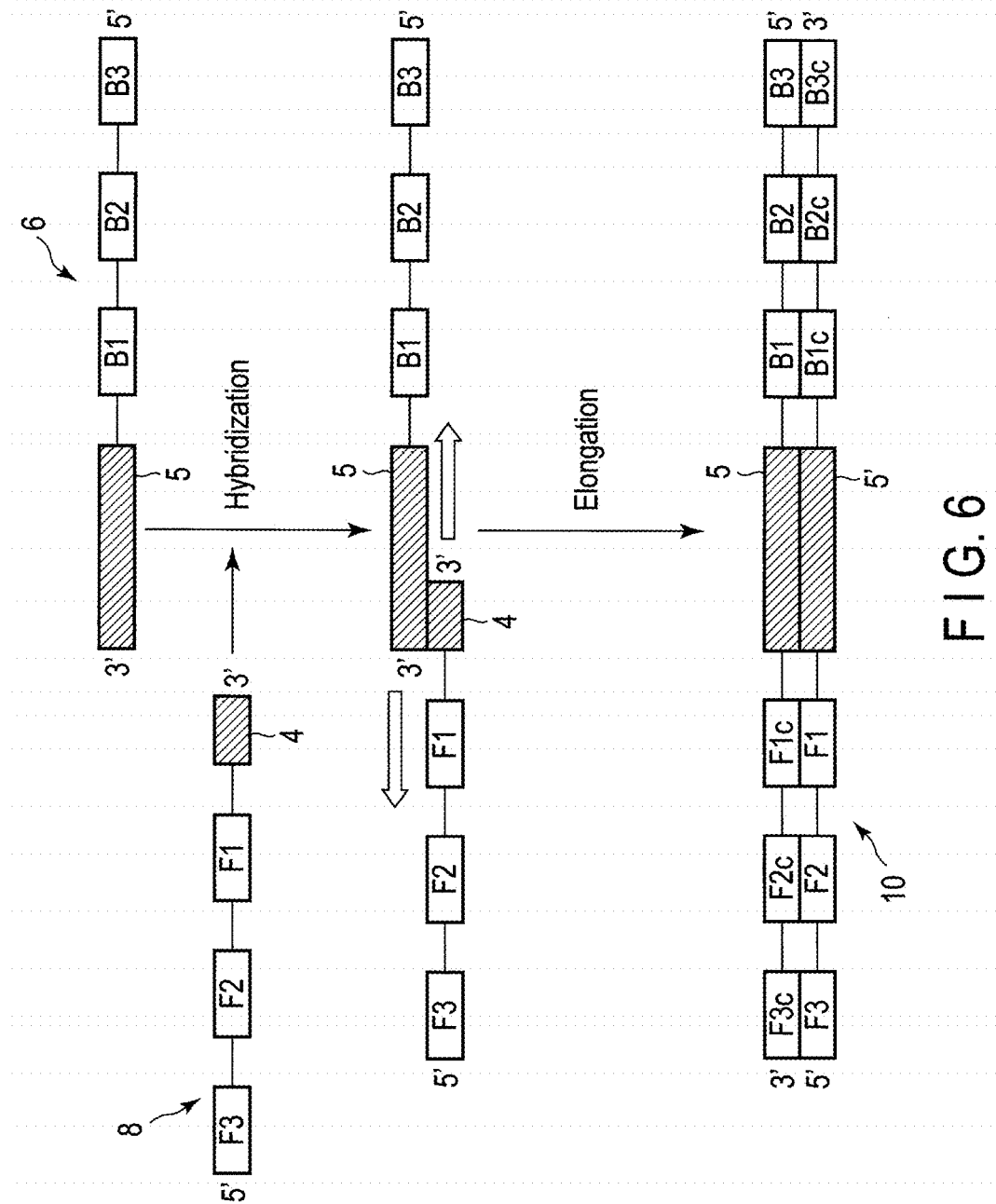
FIG. 6 is a conceptual diagram showing an example of a process of producing an elongation product.

FIG. 6 shows an example of the process of obtaining an elongation product from the reverse-transcription product 6 shown in FIG. 3, which has dissociated from the target RNA 1.

First, to a first' sequence 5 of the reverse-transcription product 6, an elongation primer sequence 9 of an elongation primer 8 hybridizes. The elongation primer 8 contains the elongation primer sequence 9 and F1 sequence, F2 sequence and F3 sequence as the second amplification sequence.

The F1 sequence, F2 sequence and F3 sequence are designed based on the LAMP primer set used in a later step, for example. The LAMP primer set contains the primers (not shown) described with reference to FIG. 3. The F2 sequence in the second amplification sequence is a complementary sequence of a sequence to which the F2 sequence of the FIP primer binds. The F3 sequence in the second amplification sequence is a complementary sequence of a sequence to which the F3 sequence of the F3 primer binds. The F1 sequence in the second amplification sequence is a sequence necessary to produce the amplification product in the LAMP reaction.

Next, with the DNA polymerase, the elongation primer 8 and the reverse-transcription product 6 elongate while utilizing each other as a template. That is, the 3' terminal of the elongation primer 8 elongates using the reverse-transcription product 6 as the template, and at the same time, the 5' terminal of the reverse-transcription product 6 elongates using the elongation primer 8 as the template (as indicated by a hollow arrow). As a result, an elongation product 10 of double-stranded DNA is produced. The elongation product 10 contains, in one chain, F1c to F3c sequences complementary to the F1 to F3 sequences, respectively, the first' sequence 5 and B1 to B3 sequences, and in the other chain, F1 to F3 sequences, a sequence 11 complementary to the first' sequence 5 and B1c to B3c sequences complementary to the B1 to B3 sequences, respectively.

In step (d), the amplification reaction liquid containing the elongation product obtained in step (c), the primer set to be bound to the elongation product and at least one of Tin(exo-) DNA polymerase and Bsm DNA polymerase is maintained under the amplification reaction conditions, thereby amplifying the first' sequence and/or its complementary sequence by using the elongation product as the template.

The ingredients for the amplification reaction contained in the amplification reaction liquid will be described.

The elongation product is one obtained in step (c).

The primer set to be bound to the elongation product is a set of primers necessary for amplifying the first' sequence or complementary sequence thereof by using the elongation product as a template. The primer set to be bound to an elongation product may be, for example, an isothermal amplification primer set. The isothermal amplification primer set contains at least the first primer for binding to the first amplification sequence or its complementary sequence and the second primer for binding to the second amplification sequence or its complementary sequence.

The primer set to be bound to the elongation product may be designed, when the base sequences of the reverse-transcription primer and the elongation primer are predetermined, based on the base sequences of the reverse-transcription primer and the elongation primer and the type of the amplification method employed according to the common knowledge of a person skilled in the art. When designing the base sequence of the primer set to be bound to an elongation product before determining the base sequences of the reverse-transcription primer and the elongation primer, the primer set to be bound to the elongation product may be designed based on the type of the amplification method employed according to the common knowledge of a person skilled in the art, and the base sequences of the reverse-transcription primer and the elongation primer may be determined based thereon.

Figure 7:
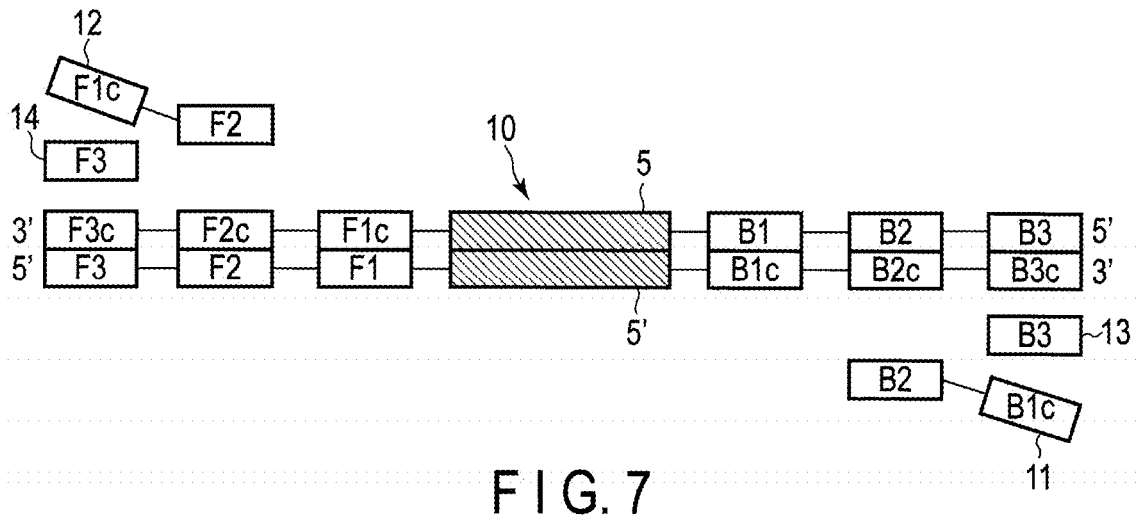
FIG. 7 is a schematic diagram showing elongation products and primers which respectively correspond to each other.

FIG. 7 shows an example of the primer set to be bound to the elongation product. The primer set be bound to the elongation product, shown in FIG. 7 is for amplifying the first' sequence 5 and its complementary sequence 5' of the elongation product 10 shown in FIG. 6. In this example, the primer set to be bound to an elongation product is an isothermal amplification primer set, and contains a BIP primer 11, FIP primer 12, B3 primer 13 and F3 primer 14. The BIP primer 11 contains a B2 sequence and a B1c sequence, and the B2 sequence and B1c sequence are linked in this order from the 3' toward the 5' direction. The B2 sequence is a sequence for binding to the B2c sequence contained in the complementary sequence of the first amplification sequence. The B1c sequence is a sequence complementary to the B1 sequence. The FIP primer 12 contains an F2 sequence and an F1c sequence, and the F2 sequence and F1c sequence are linked in this order from the 3' toward the 5' direction. The F2 sequence is a sequence for binding to the F2c sequence contained in the complementary sequence of the second amplification sequence. The F1c sequence is a sequence complementary to the F1 sequence. The B3 primer 13 contains a B3 sequence. The F3 primer 14 contains an F3 sequence. Even without the F3 region or B3 region, the reaction occurs. The B2 sequence of the BIP primer is a sequence for binding to the complementary sequence of the B2 sequence in the first amplification sequence. The F2 sequence of the FIP primer is a sequence for binding to the complementary sequence of the F2 sequence in the second amplification sequence. Therefore, the primer set to be bound to an elongation product, shown in FIG. 7 contains a BIP primer as the first primer and an FIP primer as the second primer.

Tin(exo-) DNA polymerase and Bsm DNA polymerase are each an enzyme for catalyzing the amplification reaction which amplifies the first' sequence and its complementary sequence using the elongation product as the template. Tin(exo-) DNA polymerase and Bsm DNA polymerase each should only be a conventionally known Strand displacement enzyme generally called by these names. The amplification reaction liquid contains Tin(exo-) DNA polymerase, Bsm DNA polymerases, or a combination of these. The concentration of these enzyme in the amplification reaction liquid may be 2 U to 32 U.

With use of Tin(exo-) DNA polymerase, Bsm DNA polymerases or a combination of these as the enzyme catalyzing the amplification reaction, it is possible to more specifically amplify the full length of the elongation product containing the first' sequence and the complementary sequence. That is, for example, in the reverse-transcription reaction of step (a) and the elongation reaction of step (c), a nonspecific product which do not contain the first' sequence and its complementary sequence or contain only a portion thereof, if any, can be produced in addition to the target reverse-transcription product and elongation product. If such a nonspecific product is amplified, an amplification product that contains a low concentration of the original target amplification product containing the full length of the first' sequence and the complementary sequence may be undesirably generated. In this case, it is difficult to detect the target RNA with sufficient accuracy. However, with the method of the embodiment, with use of Tin(exo-) DNA polymerase and/or Bsm DNA polymerase it is possible to suppress the amplification of the nonspecific product and obtain an amplification product which contains sequences of the original target object of the amplification more. Thus, with use of these enzymes, it becomes possible to specifically amplify an RNA whose content in the sample is very low, which is difficult with the conventional technique. Thus, an RNA amplification method with simpler procedure, higher sensitivity and specificity can be provided by a. Further, with use of these enzymes, the target RNA can be specifically amplified even under such a condition that a great number of nonspecific products are present. Therefore, steps (a) to (d) can be carried out in the reaction liquid which serves as all of the reverse-transcription reaction liquid, elongation reaction liquid and amplification reaction liquid, without removing the nonspecific products generated by the reverse-transcription reaction and elongation reaction, or separating the reverse-transcription products for the elongation reaction, or separating the elongation products for the amplification reaction, as will be described in detail later. Thus, a further simpler RNA amplification method can be provided.

The amplification reaction liquid may contain, in addition to these ingredients, a desired ingredient necessary for the amplification reaction. Such an ingredient may be, for example, a substrate such as deoxynucleoside triphosphates (dNTPs) or a salt for maintaining an appropriate environment for the amplification or the like.

The condition for the amplification reaction may be selected depending on the type of the primer or the like based on the common knowledge of a person skilled in the art. The condition for the amplification reaction may be, for example, an isothermal amplification condition, which may be, for example, an isothermal temperature of 50° C. to 70° C. for 15 to 90 minutes.

By maintaining the amplification reaction liquid under the amplification reaction condition, the first' sequence and/or its complementary sequence are amplified by using the elongation product as the template.

With the RNA amplification method of the embodiment, the target RNA in a sample can be amplified more simply, with higher sensitivity and specificity.

In a further embodiment, the DNA polymerase contained in the elongation reaction liquid of step (c) may contain at least one of Tin(exo-) DNA polymerase and Bsm DNA polymerase, or a combination of these. In that case, the DNA polymerase used in step (c) may be used for the amplification reaction in step (d). That is, for example, Tin(exo-) DNA polymerase, Bsm DNA polymerase or a combination thereof may be contained as DNA polymerase in the elongation reaction liquid and step (d) may be carried out after finishing the elongation reaction without adding the enzyme for the amplification to the amplification reaction liquid. In this manner, the amount of the enzyme used can be decreased, thereby reducing the cost. Further, the procedure of the test can be more facilitated.

The reverse-transcription reaction, elongation reaction and amplification reaction, described above can be carried out in the reaction liquid which serves as all of the reverse-transcription reaction liquid, elongation reaction liquid and amplification reaction liquid. That is, for example, an ingredient necessary for the elongation reaction and amplification reaction may be added in advance to the reverse-transcription reaction liquid before carrying out the reverse-transcription reaction, or after each reaction, an ingredient necessary for the next reaction may be added to the reaction liquid, so as to be used in the next reaction. Or, after each reaction, all or part of the reaction liquid may be added to the solution containing an ingredient necessary for the next reaction. In that case, it is not necessary to remove the nonspecific product produced by the reverse-transcription reaction and elongation reaction, separate the reverse-transcription product for the elongation reaction, or separate the elongation product for the amplification reaction or the like, and thus the operation is simpler. This can be achieved by using Tin(exo-) DNA polymerase or Bsm DNA polymerase which can amplify the target product specifically even under the condition where a nonspecific product exists, in the amplification reaction.

2. RNA Detection Method

According to a further embodiment, a target RNA detection method is provided.

Figure 8:
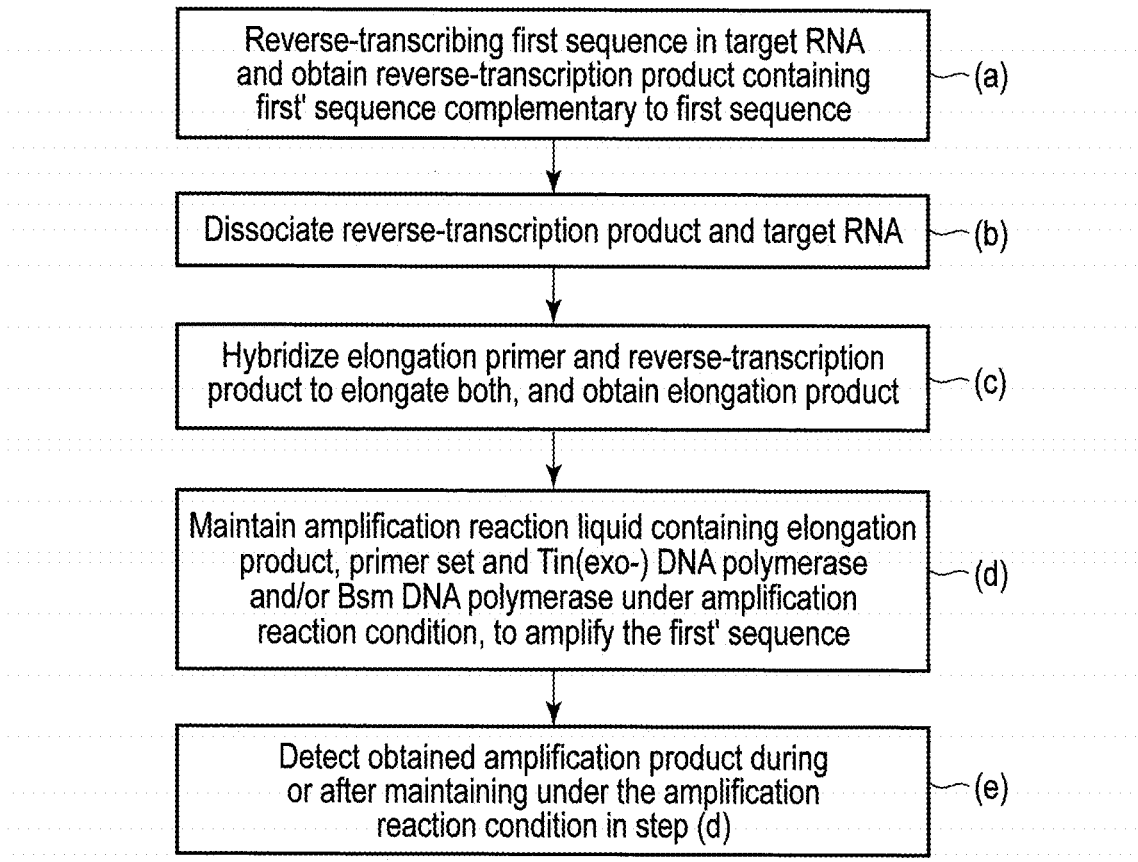
FIG. 8 is a flowchart illustrating an example of an RNA detection method of an embodiment.

FIG. 8 shows a flow schematically showing an example of the RNA detection method of the embodiment. The RNA detection method of the embodiment comprising executing steps (a) to (d) of the RNA amplification method of the embodiment, and detecting (step (e)) an amplification product obtained during or after maintaining under the amplification reaction condition in step (d).

The detection of an amplification product can be carried out based on, for example, turbidity, fluorescence, electrochemical signal or the like as an indicator. The detection of the amplified product using turbidity as an indicator may be performed, for example, by a turbidimeter, an absorption spectrometer, visual observation or the like. The detection of the amplified product using fluorescence as an indicator may be performed, for example, by detecting the fluorescence generated using a reagent that produces fluorescence, such as a fluorescence reagent containing calcein or intercalater, depending on the presence of the amplified product or the amplification reaction. The detection of the amplified product using electrochemical signal as an indicator may be performed, for example, by detecting the signal generated using a reagent that produces an electrochemical signal of a redox reaction or the like, such as an intercalator, depending on the presence of the amplified product or the amplification reaction. The detection of an amplification product may be carried out at a specific time from the start of the amplification reaction or may be carried out with time. The term "with time" may be interpreted as continuously or intermittently, in which the detection is carried out at a plurality of times at predetermined intervals.

Further, the detection of the amplification reaction and/or the amplification product can be carried out by detecting the hybridization between the amplification product and the probe. The hybridization may be detected by a probe-immobilized substrate. The probe-immobilized substrate comprises a substrate and a plurality of types of probes immobilized on the substrate. The probes may each include the same sequence as that of each respective detection region, or its complementary sequence. With the above-described configuration, a probe is hybridized with an amplification product containing the corresponding sequence. The presence of the amplification product or the amount thereof is detected by sensing the hybridization. Thus, in the detection method, the presence of a target nucleic acid in a sample or the amount thereof is detected.

The probe-immobilized substrates may be interpreted as synonyms of such terms generally used, as "DNA chip" and "DNA array" in a narrow sense, for example, and may be used exchangeably among them. Further, for example, devices such as a cassette for detection and a cartridge, which are prepared by integrating, for example, a small-sized probe-immobilized substrate such as a DNA chip and other structural members necessary to form an amplification reaction unit, a passage, etc., into one unit may be interpreted also as probe-immobilized substrates. In that case, the amplification reaction and/or detection may be automatically carried out by a device which can automatically control the temperature within the DNA chip and/or transferring of the sample and the reaction liquid, etc.

From the results of the detection, the presence of the target RNA in the sample and/or the amount thereof can be determined. These items are determined, for example, by measuring the time required until the turbidity or fluorescence exceeds a predetermined threshold as the rise time. When the target RNA is present, a rise of the increase in turbidity or fluorescence is observed at an earlier point. Or, the concentration of the target RNA can be determined based on the rise time. Or, the concentration of the target RNA can be determined by, for example, preparing a calibration curve from measurement results of a plurality of different reference samples whose amounts of target RNA present are already known and comparing the detection results with the calibration curve.

In the further embodiment of the RNA detection method, the first' sequence and its complementary sequence may be separated from other sequences by fragmenting the amplification product with a specific restriction enzyme, and the first' sequence and its complementary sequence may be detected. In that case, the reverse-transcription primer, elongation primer and primer sets to be bound to elongation product, are designed so that the amplification product includes a sequence which can be broken by a specific restriction enzyme. After the amplification reaction, the amplification product is treated with a corresponding restriction enzyme, and then subjected to, for example, electrophoresis. When it is found that the target RNA is present in the sample and the sequence containing the first' sequence and its complementary sequence is present in an amplification product, by the electrophoresis, the product appears as one band in a specific position. Thus, the presence/absence of a target RNA in a sample can be judged more clearly.

According to the RNA detection method of the embodiment, a target RNA can be detected simply, with high sensitivity and specifically.

Further, when the target RNA is, for example, an RNA to be expressed or whose amount of expression increases or decreases in a cell afflicted with a specific disease, by detecting the target RNA using the detection method of the embodiment, it is possible to determine whether or not a living organism, from which a sample is extracted, is afflicted with a specific disease more simply, with higher sensitivity and specificity. Examples of the specific disease may be cancers such as breast cancer, colorectal cancer or lung cancer, or other diseases. Or, for example, when the target RNA is an RNA to be expressed, or whose amount of expression increases or decreases in specific bacteria or virus, by detecting the target RNA using the detection method of the embodiment, it is possible to determine the presence of specific bacteria or virus of a sample or whether or not the living organism, from which a sample is extracted, is infected by specific bacteria or virus, more simply, with higher sensitivity and specificity.

3. Assay Kit

According to an embodiment, an assay kit for amplifying or detecting a target RNA containing the first sequence in a sample is provided.

The assay kit of the embodiment comprises a reverse-transcription primer, reverse transcriptase, an elongation primer, a primer set to be bound to an elongation product, and Tin(exo-) DNA polymerase, Bsm DNA polymerase or a combination thereof. The assay kit may contain a further ingredient necessary for the reverse-transcription reaction, elongation reaction and/or amplification reaction.

The assay kit may further contain a DNA polymerase different from Tin(exo-) DNA polymerase or Bsm DNA polymerase.

The ingredients are those described above. The ingredients may be separately contained in respective containers or combinations of any of these or all the ingredients may be contained in the same container.

According to such an assay kit, it is possible to detect the target RNA more simply, with higher sensitivity and specificity.

EXAMPLES

Example 1 (Comparative Example): Detection of RNA by the LAMP Method Using Gsp SSD DNA Polymerase, Bst DNA Polymerase and Bst2.0 DNA Polymerase (1) Reverse-Transcription Reaction First, a plurality of reverse-transcription reaction liquids (20 μL) of different concentrations of synthetic miRNA (1E+3, 1E+4, 1E+5, 1E+6, and 0 copy) were prepared. The reverse-transcription reaction liquids contain, in addition to the respective synthetic miRNAs, 5 nM of reverse-transcription primer, 20 mM of Tris-HCl (pH: 8.8), 50 mM of KCl, 8 mM of $MgCl_2$, 10 mM of $(NH_4)_2SO_4$, 0.1% of Tween-20, 0.8 M of betaine, 1.4 mM of each of dNTPs, 1 mM of DTT and 4 U of RNaseOUT all at the final concentration. Each of the reverse-transcription reaction liquids was maintained at 16° C. for 30 minutes, 42° C. for 30 minutes and 85° C. for 5 minutes, and the reverse-transcription reaction was allowed to occur.

(2) Elongation Reaction

Then, to each of the reverse-transcription reaction liquids, 4.45 nM of the elongation primer and 0.4 U of DeepVent (exo-) were added to prepare elongation reaction liquids. Each of the elongation reaction liquids was maintained at 95° C. for 2 minutes, and subjected to 35 cycles of the maintenance (at 95° C. for 20 seconds, 55° C. for 30 seconds and 72° C. for 30 seconds), followed by the maintenance at 72° C. for 5 minutes, thereby allowing the elongation reaction to occur.

(3) LAMP Reaction

To each of the liquids respectively containing, all at the final concentration, 20 mM of Tris-HCl (pH: 8.8), 50 mM of KCl, 8 mM of $MgCl_2$, 10 mM of $(NH_4)_2SO_4$, 0.1% of Tween-20, 0.8 M of betaine, 1.4 mM of each of dNTPs, 1.6 μM of the FIP primer, 1.6 μM of the BIP primer, 0.8 μM of the LF primer, 8 U of Gsp SSD DNA polymerase, the elongation reaction liquid (10 μL) obtained after the elongation reaction was added, to prepare a plurality of 25 μL of LAMP reaction liquids. As a positive control, a reaction liquid containing synthetic DNA (1E+5 copies) containing a sequence of the target elongation product was prepared. As a negative control, a solution not containing any nucleic acid strand was prepared. Each of the LAMP reaction liquids, positive control and negative control were maintained at 65° C. for 90 minutes, to allow the LAMP reaction to occur. For each of the liquids, the turbidity was measured with time.

Similarly, a LAMP reaction liquid containing Bst DNA polymerase or Bst2.0 DNA polymerase as the DNA polymerase was prepared and subjected to the amplification reaction and the detection of turbidity similarly.

(4) Electrophoresis

Subsequently, each of the reaction liquids was treated with the restriction enzyme HinfI to fragment the amplification product, and then subjected to electrophoresis. The above-described test was carried out with two tubes (two repetitions) per one type of reaction liquid. The results are shown in FIG. 9.

FIG. 9 shows the results with Gsp SSD DNA polymerase in part (a), Bst DNA polymerase in part (b) and Bst2.0 DNA polymerase in part (c). Each part of the figure indicates the time to threshold of turbidity (hereinafter "Tt") of each of the reaction liquids described above and the electropherogram.

The same band pattern as that of the positive control (PC) was obtained only with reaction liquids containing 1E+6 copies (10^6) of miRNA when Gsp SSD DNA polymerase and Bst2.0 DNA polymerase were used, and only with reaction liquids containing 1E+6 or more (10^5) copies of miRNA when Bst DNA polymerase was used. Even with any of these enzymes, when the concentration of miRNA is lower than a concentration in which the same band pattern as that of the positive control (PC) was obtained, the amplification product was produced (the rise in turbidity occurred), but the sequence of miRNA, the target, was not specifically amplified.

Figure 10:
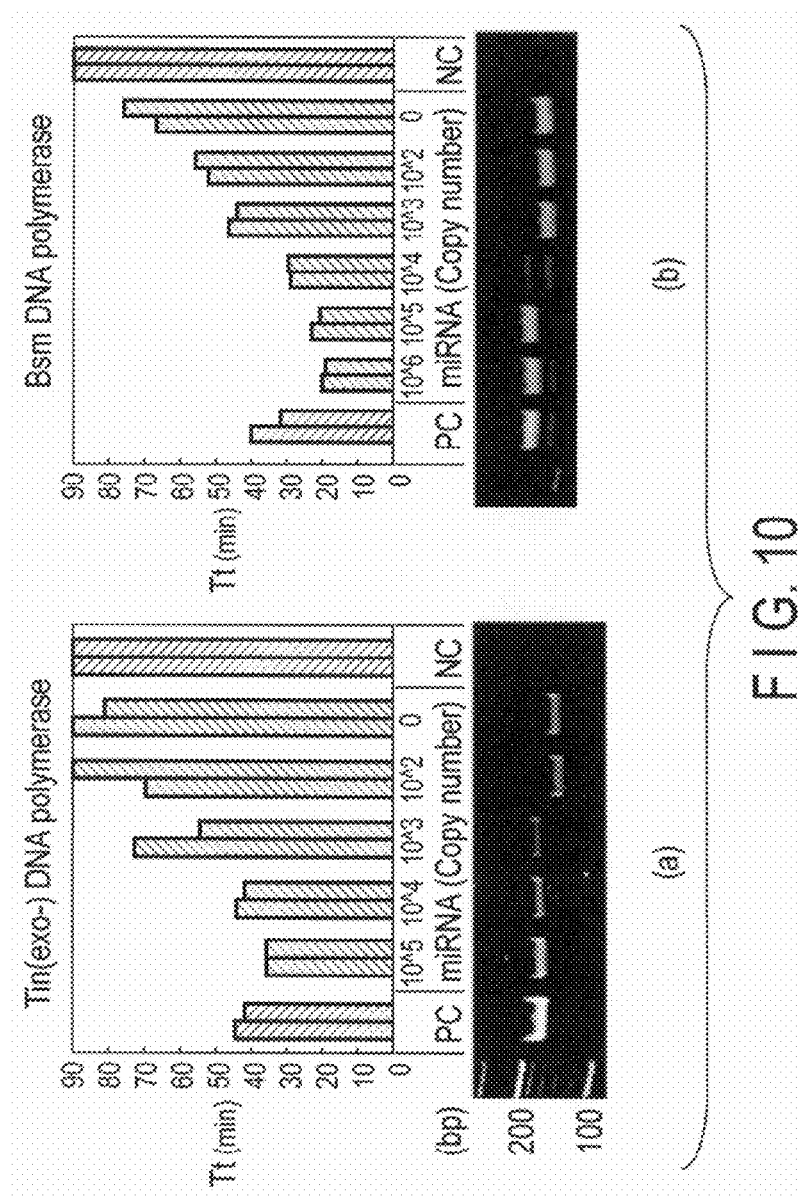
FIG. 10 includes graphs and electropherograms showing test results of Example 2.

Example 2 (the Embodiment): Detection of Short-Chain RNA by the LAMP Method Using Tin(Exo-) DNA Polymerase or Bsm DNA Polymerase With a method similar to that of the comparative example, miRNA was reverse-transcribed, elongated and amplified using Tin(exo-) DNA polymerase or Bsm DNA polymerase as the LAMP enzyme. The results are shown in FIG. 10. FIG. 10 shows the results with Tin(exo-) DNA polymerase in part (a) and those of Bsm DNA polymerase in part (b). Each part of the figure indicates the Tt value of each of the reaction liquids described above and the electropherogram.

The same band pattern as that of the positive control (PC) was obtained with reaction liquids containing 1E+5 copies (10^5), 1E+4 copies (10^4) and 1E+3 copies (10^3) of miRNA when Tin(exo-) DNA polymerase was used, and with reaction liquids containing 1E+6 copies (10^6), 1E+5 copies (10^5) and 1E+4 copies (10^4) of miRNA when Bsm DNA polymerase was used. Thus, it has been clarified that the target gene can be specifically amplified from a reaction liquid with less concentration of miRNA in the case which uses Tin(exo-) DNA polymerase or Bsm DNA polymerase than the case where Gsp SSD DNA polymerase, Bst DNA polymerase or Bst2.0 DNA polymerase was used.

Example 3: Evaluation in Amplifiability and Specificity of Amplification of 11 Types of Strand Displacement Enzymes As to 11 types of Strand displacement enzymes (including those used in Examples 1 and 2) each generally known to have a high detection sensitivity and a high amplification speed or to be specifically amplifiable when amplifying long chain DNA (which need not be reverse-transcribed and elongated) in the sample, a test similar to that of the comparative example described above was carried out using each as the LAMP enzyme, and the presence/absence and specificity of the amplification were evaluated. The results are shown in Table 1.

TABLE 1

|  | Strand displacement enzyme | Amplification | Specific amplification |
|---|---|---|---|
| Comparative example | Gsp SSD DNA polymerase | + | − |
|  | Bst DNA polymerase | + | − |
|  | Csa DNA polymerase | + | − |
|  | 96-7 DNA polymerase | − |  |
|  | OmniAmp DNA polymerase | − |  |
|  | Bst2.0 WarmStart DNA polymerase | + | − |
|  | Bst3.0 DNA polymerase | + | − |
|  | Displace Ace DNA polymerase | − |  |
|  | SD polymerase | − |  |
|  | TOPOTAQ DNA polymerase | − |  |
| Embodiments | Tin(exo-) DNA polymerase | + | + |
|  | Bsm DNA polymerase | + | + |

In the table, the item "Presence/absence of amplification" indicates the result of turbidity measurement, in which the sign "+" means that the rise in turbidity was observed when the concentration of synthetic miRNA is was 10^5 copies/25 μL, and the sign "−" means that the rise in turbidity was not observed and therefore the amplification could not achieved. The item "specific amplification" indicates the result of electrophoresis, in which the sign "+" means that the specific amplification was possible under the condition that the concentration of miRNA is 10^4 copies/25 μL or less, and the sign "−" means that the specific amplification was not possible under the above-indicated condition. Note that those of the samples in which the amplification could not be achieved were not subjected to electrophoresis. The results shown in Table 1 show that with Tin(exo-) DNA polymerase or Bsm DNA polymerase, specific amplification was possible in a reaction liquid containing 1E+4 (10^4) copies of miRNA or less.

It has been found from these test that with Tin(exo-) DNA polymerase or Bsm DNA polymerase, such a method is provided that miRNA, which is contained in a very small amount in a sample, of a short-chain and easily decomposable, can be amplified and detected simply with high sensitivity and specificity.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A method of amplifying a target RNA containing a first sequence, in a sample, the method comprising:
   (a) reverse-transcribing the first sequence in the target RNA using a reverse-transcription primer which contains a reverse-transcription primer sequence and a first amplification sequence, thereby obtaining a reverse-transcription product containing a first' sequence complementary to the first sequence;
   (b) dissociating the reverse-transcription product and the target RNA from each other;
   (c) hybridizing an elongation primer and the reverse-transcription product to elongate the elongation primer and the reverse-transcription product, thereby obtaining a double-stranded DNA elongation product which contains the first' sequence and/or a complementary sequence thereof, wherein the elongation primer contains an elongation primer sequence complementary to a continuous sequence containing a 3' terminal region of the reverse-transcription product and a second amplification sequence; and
   (d) maintaining an amplification reaction liquid containing the elongation product, a LAMP primer set to be bound to the elongation product, and Tin(exo-) DNA polymerase under a LAMP amplification reaction condition, thereby amplifying the first' sequence and/or the complementary sequence thereof using the elongation product as a template.

2. The method of claim 1, wherein the reverse-transcribing product of step (a) is obtained by maintaining a reverse-transcription reaction liquid under a reverse-transcription reaction condition, where the reverse-transcription reaction liquid includes the sample, a reverse transcriptase, and the reverse-transcription primer.

3. The method of claim 1, wherein the elongation product of step (c) is obtained by maintaining an elongation reaction liquid under an elongation reaction condition, where the elongation reaction liquid includes the reverse-transcription product, DNA polymerase, and the elongation primer to hybridize the elongation primer and the reverse-transcription product, thereby elongating the elongation primer and the reverse-transcription product using each other as a template.

4. The method of claim 3, wherein the elongation product is a double-stranded DNA, where one of strands of the elongation product contains a complementary sequence to the second amplification sequence, the first' sequence and the first amplification sequence, and an other strand of the elongation product contains the second amplification sequence, a complementary sequence to the first' sequence and a complementary sequence to the first amplification sequence.

5. The method of claim 3, wherein the LAMP primer set bound to the elongation product includes at least a first primer to be bound to the first amplification sequence of the elongation product or a complementary sequence thereof and a second primer to be bound to the second amplification sequence of the elongation product or a complementary sequence thereof.

6. The method of claim 1, wherein the target RNA is a short-chain RNA.

7. The method of claim 3, wherein the DNA polymerase is Tin(exo-) DNA polymerase.

8. A method of detecting a target RNA containing a first sequence, in a sample, the method comprising:
   executing the steps (a) to (d) of the RNA amplification method according to claim 1; and
   (e) detecting the obtained amplification product during or after maintaining the reaction liquid under the amplification reaction condition in step (d).

9. An assay kit for amplifying or detecting a target RNA containing a first sequence, in a sample according to the method of claim 1, the kit comprising:
   the reverse-transcription primer for reverse-transcribing the first sequence;
   a reverse transcriptase;
   the elongation primer for obtaining an elongation product;
   a LAMP primer set to be bound w the elongation product, containing a primer to be bound to the elongation product; and
   Tin(exo-) DNA polymerase.

10. The assay kit of claim 9, wherein
   the reverse-transcription primer is for reverse-transcribing the first sequence to obtain a reverse-transcription product containing the first' sequence complementary to the first sequence;
   the elongation primer is for hybridizing with the reverse-transcription product to elongate the elongation primer and the reverse-transcription product by using each other as a template, and obtain an elongation product in which one of strands contains a complementary sequence to the second amplification sequence, the first' sequence and the first amplification sequence, and an other strand contains the second amplification, a complementary sequence to the first' sequence and a complementary sequence to the first amplification sequence; and
   the LAMP primer set to be bound to the elongation product contains a first primer to be bound to the first amplification sequence of the elongation product or a complementary sequence thereof, and a second primer to be bound to the second amplification sequence of the elongation product or a complementary sequence thereof.

11. The assay kit of claim 9, further comprising:
   DNA polymerase different from Tin(exo-) DNA polymerase and Bsm DNA polymerase.

12. The assay kit of claim 9, wherein the LAMP primer set to be bound to the elongation product is an isothermal amplification LAMP primer set.

13. The method of claim 1, wherein the first amplification sequence comprises B1 sequence and B2 sequence, and the second amplification sequence comprises F1 sequence and F2 sequence, wherein
the B1 sequence, the B2 sequence, the F1 sequence, and the F2 sequence, and B1c sequence, B2c sequence, F1c sequence, and F2c sequence, as their complementary sequences respectively, are for the LAMP primer set to bind,
the LAMP primer set includes at least a FIP primer and a BIP primer,
the FIP primer comprises the F2 sequence and the F1c sequence, and
the BIP primer comprises the B2 sequence and the B1c sequence.

14. The method of claim 13, wherein the first amplification sequence further comprises B3 sequence, and the second amplification sequence further comprises F3 sequence, wherein
the B3 sequence and B3c sequence, and the F3 sequence and F3c sequence, as their complementary sequences respectively, are for the LAMP primer set to bind,
the LAMP primer set further includes a B3 primer and a F3 primer, the B3 primer comprises the B3 sequence, and the F3 primer comprises the F3 sequence.

15. The method of claim 8, wherein the reverse-transcribing product of step (a) is obtained by mintaining a reverse-transcription reaction liquid under a reverse-transcription reaction condition, where the reverse-transcription reaction liquid includes the sample, a reverse transcriptase, and the reverse-transcription primer.

16. The method of claim 8, wherein the elongation product of Step (c) is obtained by maintaining an elongation reaction liquid under an elongation reaction condition, where the elongation reaction liquid includes the reverse-transcription product, DNA polymerase, and the elongation primer to hybridize the elongation primer and the reverse-transcription product, thereby elongating the elongation primer and the reverse-transcription product using each other as a template.

17. The method of claim 16, wherein the elongation product is a double-stranded DNA, where one of strands of the elongation product contains a complementary sequence to the second amplification sequence, the first' sequence and the first amplification sequence, and an other strand of the elongation product contains the second amplification sequence, a complementary sequence to the first' sequence and a complementary sequence to the first amplification sequence.

18. The method of claim 16, wherein the LAMP primer set bound to the elongation product includes at least a first primer to be bound to the first amplification sequence of the elongation product or a complementary sequence thereof and a second primer to be bound to the second amplification sequence of the elongation product or a complementary sequence thereof.

19. The method of claim 8, wherein the target RNA is a short-chain RNA.

20. The method of claim 16, wherein the DNA polymerase is Tin(exo-) DNA polymerase.

21. The method of claim 8, wherein the first amplification sequence comprises B1 sequence and B2 sequence, and the second amplification sequence comprises F1 sequence and F2 sequence,
wherein
the B1 sequence, the B2 sequence, the F1 sequence and the F2 sequence, and B1c sequence, B2c sequence, F1c sequence and F2c sequence, as their complementary sequences respectively, are for the LAMP primer set to bind,
the LAMP primer set includes at least a FIP primer and a BIP primer,
the FIP primer comprises the F2 sequence and the F1c sequence, and
the BIP primer comprises the B2 sequence and the B1c sequence.

22. The method of claim 21, wherein the first amplification sequence further comprises B3 sequence, and the second amplification sequence further comprises F3 sequence, wherein
the B3 sequence and B3c sequence, and the F3 sequence and F3c sequence, as their complementary sequences respectively, are for the LAMP primer set to bind,
the LAMP primer set further includes a B3 primer and a F3 primer, the B3 primer comprises the B3 sequence, and the F3 primer comprises the F3 sequence.

23. The kit of claim 9, wherein the LAMP primer set includes at least a FIP primer and a BIP primer, the FIP primer comprises the F2 sequence and the F1c sequence, and the BIP primer comprises the B2 sequence and the B1c sequence.

24. The kit of claim 23, wherein the LAMP primer set further includes a B3 primer and a F3 primer, the B3 primer comprises the B3 sequence, and the F3 primer comprises the F3 sequence.

* * * * *